(12) United States Patent
Ritter et al.

(10) Patent No.: US 10,031,078 B2
(45) Date of Patent: *Jul. 24, 2018

(54) DISTANCE SENSING BY IQ DOMAIN DIFFERENTIATION OF TIME OF FLIGHT (TOF) MEASUREMENTS

(71) Applicant: Intersil Americas LLC, Milpitas, CA (US)

(72) Inventors: David W. Ritter, San Jose, CA (US); Itaru Hiromi, Cambridge, MA (US)

(73) Assignee: INTERSIL AMERICAS LLC, Milpitas, CA (US)

( * ) Notice: Subject to any disclaimer, the term of this patent is extended or adjusted under 35 U.S.C. 154(b) by 913 days.

This patent is subject to a terminal disclaimer.

(21) Appl. No.: 14/296,277

(22) Filed: Jun. 4, 2014

(65) Prior Publication Data

US 2014/0327900 A1    Nov. 6, 2014

Related U.S. Application Data

(63) Continuation of application No. 12/979,726, filed on Dec. 28, 2010, now Pat. No. 8,760,631.

(Continued)

(51) Int. Cl.
   *G01S 17/08*     (2006.01)
   *G01N 21/55*     (2014.01)
   (Continued)

(52) U.S. Cl.
   CPC ............... *G01N 21/55* (2013.01); *G01J 1/46* (2013.01); *G01J 9/00* (2013.01); *G01S 17/08* (2013.01); *H01L 31/101* (2013.01)

(58) Field of Classification Search
   CPC .... G01N 21/55; G01J 9/00; G01J 1/46; G01S 17/08; H01L 31/101
   See application file for complete search history.

(56) References Cited

U.S. PATENT DOCUMENTS 3,878,536 A    4/1975    Pedersen
3,996,590 A    12/1976   Hammack
(Continued)

FOREIGN PATENT DOCUMENTS

CN    1110397 A    10/1995
CN    1483268 A    3/2004
(Continued)

OTHER PUBLICATIONS

Office Action dated Jul. 19, 2013, in Taiwanese Patent Appl. No. 100103040 filed Jan. 27, 2011.
(Continued)

*Primary Examiner* — Luke D Ratcliffe
*Assistant Examiner* — Vicente Rodriguez
(74) *Attorney, Agent, or Firm* — Foley & Lardner LLP

(57) ABSTRACT

A system and method for identifying a position of a moving object, regardless of static objects present in the optical field of an active infrared (IR) proximity detector, is provided. Moreover, a modulated light emitting diode (LED) signal is captured and processed through I/Q demodulation. Specifically, the reflections received at an IR sensor are demodulated to generate in-phase (I) and quadrature phase (Q) signals and the derivative of I/Q signals is obtained to isolate motion. For example, an I/Q domain differentiator or a high pass filter is employed to calculate the derivative, which actively remove the effects of all forms of static interference. Further, the phase of the derivative I/Q signals is determined and is utilized to reconstruct the distance at which the motion occurred.

16 Claims, 8 Drawing Sheets

Related U.S. Application Data

(60) Provisional application No. 61/298,895, filed on Jan. 27, 2010.

(51) Int. Cl.
  *G01J 1/46* (2006.01)
  *G01J 9/00* (2006.01)
  *H01L 31/101* (2006.01)

(56) References Cited

U.S. PATENT DOCUMENTS

| | | | |
|---|---|---|---|
| 4,458,212 A | 7/1984 | Brehmer et al. | |
| 4,542,475 A | 9/1985 | Acampora | |
| 4,551,710 A | 11/1985 | Troup et al. | |
| 4,644,341 A | 2/1987 | Warner | |
| 4,648,364 A | 3/1987 | Wills | |
| 4,942,561 A | 7/1990 | Oshishi et al. | |
| 5,055,671 A | 8/1991 | Jones | |
| 5,121,199 A | 6/1992 | Aoki | |
| 5,563,701 A | 10/1996 | Cho | |
| 5,593,430 A | 1/1997 | Renger | |
| 5,828,899 A | 10/1998 | Richard et al. | |
| 5,892,540 A | 4/1999 | Kozlowski et al. | |
| 5,990,409 A | 11/1999 | Takahashi et al. | |
| 6,111,256 A | 8/2000 | Shpater | |
| 6,392,539 B1 | 5/2002 | Kanasugi | |
| 6,462,726 B1 | 10/2002 | Hamada et al. | |
| 6,590,520 B1 | 7/2003 | Steele et al. | |
| 6,744,248 B2 | 6/2004 | Buchhold et al. | |
| 6,753,950 B2 | 6/2004 | Morcom | |
| 6,803,555 B1 | 10/2004 | Parrish et al. | |
| 6,819,782 B1 | 11/2004 | Imagawa et al. | |
| 6,836,212 B2 | 12/2004 | Sawinski | |
| 6,888,938 B2 | 5/2005 | Cui et al. | |
| 7,016,537 B2 | 3/2006 | Cooper | |
| 7,184,951 B2 * | 2/2007 | Royle | G10K 15/02 704/205 |
| 7,212,655 B2 | 5/2007 | Tumey et al. | |
| 7,388,655 B2 | 6/2008 | Mori | |
| 7,444,032 B2 | 10/2008 | Larkin et al. | |
| 7,486,386 B1 | 2/2009 | Holcombe et al. | |
| 7,532,870 B2 | 5/2009 | Ling | |
| 7,616,032 B2 | 11/2009 | Jang | |
| 7,619,293 B2 | 11/2009 | Hasegawa | |
| 7,620,202 B2 | 11/2009 | Fujimura et al. | |
| 7,642,501 B1 | 1/2010 | Fassbender et al. | |
| 7,714,268 B2 | 5/2010 | Leijssen et al. | |
| 8,530,819 B2 | 9/2013 | Ritter et al. | |
| 2002/0097743 A1 | 7/2002 | Baydar et al. | |
| 2003/0234341 A1 | 12/2003 | Osborn | |
| 2004/0140961 A1 | 7/2004 | Cok | |
| 2006/0120621 A1 | 6/2006 | Larkin et al. | |
| 2007/0013791 A1 | 1/2007 | Kinoshita et al. | |
| 2007/0121095 A1 | 5/2007 | Lewis | |
| 2008/0119716 A1 | 5/2008 | Boric-Lubecke et al. | |
| 2008/0205820 A1 | 8/2008 | Zheng et al. | |
| 2008/0266015 A1 | 10/2008 | Matteijssen et al. | |
| 2008/0266128 A1 | 10/2008 | Leone et al. | |
| 2009/0006730 A1 | 1/2009 | Gara et al. | |
| 2009/0027529 A1 | 1/2009 | Jung et al. | |
| 2009/0295729 A1 | 12/2009 | Kuo et al. | |
| 2011/0180693 A1 | 7/2011 | Ritter et al. | |
| 2011/0180709 A1 | 7/2011 | Craddock et al. | |
| 2011/0181861 A1 | 7/2011 | Ritter et al. | |
| 2011/0182519 A1 | 7/2011 | Craddock et al. | |

FOREIGN PATENT DOCUMENTS

| | | | |
|---|---|---|---|
| CN | 1619295 A | 5/2005 | |
| CN | 1667432 A | 9/2005 | |
| CN | 101581783 A | 11/2009 | |
| JP | 2909742 B2 | 6/1999 | |
| JP | 2005-249764 A | 9/2005 | |
| JP | 2010-127739 A | 6/2010 | |
| TW | 494616 B | 7/2002 | |
| TW | 439716 B | 6/2014 | |
| WO | 198704034 A1 | 7/1987 | |
| WO | WO01/55746 A1 | 8/2001 | |
| WO | 2009088662 A2 | 7/2009 | |

OTHER PUBLICATIONS

Ryan et al., "A Long-Range, Wide Field-of-View Infrared Eyeblink Detector", Journal of Neuroscience Methods 152 (2006) 74-82, Apr. 2005.
Restriction dated Mar. 13, 2013, in U.S. Appl. No. 13/013,146, filed Jan. 25, 2011.
Response to Restriction filed Mar. 22, 2013, in U.S. Appl. No. 13/013,146, filed Jan. 25, 2011.
Notice of Allowance dated Jun. 3, 2013, in U.S. Appl. No. 13/013,146, filed Jan. 25, 2011.
IEEE 802.5v-2001 (Amendment to IEEE Std 802.5, 1998 Edition and IEEE Stds 802.5r and 802.5j, 1998 Edition) Nov. 16, 2001.
In-Phase & Quadrature Procedure, Radartutorial.eu, http://www.radartutorial.eu/10.processing/sp06.en.html (accesed D Sep. 16, 2011).
Office Action dated Jun. 14, 2013, in U.S. Appl. No. 13/013,199, filed Jan. 25, 2011.
Restriction dated Jun. 6, 2013, in U.S. Appl. No. 13/013,676, filed Jan. 25, 2011.
Office Action dated Dec. 13, 2012, in U.S. Appl. No. 13/013,640, filed Jan. 25, 2011.
International Search Report and Written Opinion, dated Mar. 25, 2011, for International Application No. PCT/US11/22644, 8 pages.
International Search Report and Written Opinion, dated Mar. 21, 2011, for International Application No. PCT/US11/022646, 14 pages.
International Search Report and Written Opinion, dated Apr. 6, 2011, for International Application No. PCT/US2011/022647, 17 pages.
International Search Report and Written Opinion, dated Mar. 28, 2011, for International Application No. PCT/US2011/022649, 13 pages.
International Search Report and Written Opinion, dated Mar. 28, 2011, for International Application No. PCT/US2011/022650, 10 pages.
International Search Report and Written Opinion, dated Mar. 25, 2011, for International Application No. PCT/US2011/022651, 14 pages.
Silicon Labs Si1120, "QuickSense Si1120 Proximity and Ambient Light Sensor ICs", http://www.silabs.com/products/sensors/infraredsensors/Pages/Si1120.aspx [retrieved Dec. 28, 2010].
Sharp Electronics Corporation, "GP2Y0A02YK0F Sales and Technical Information", http://www.sharpmeg.com/Page.aspx/americas/en/part/GP2Y0A02YK0F/ [retrieved Dec. 28, 2010].
Theodore D. Rees, "Long Range Proximity and/or Motion Detector With Ambient Light Detection Capabilities", U.S. Appl. No. 61/173,951, filed Apr. 29, 2009.
David Stoppa et al. "An 80×60 Range Image Sensor Based on 10μm 50MHz Lock-In Pixels in 0.18μm CMOS", ISSCC 2010/ Session 22 / Image Sensors / 22.7, 2010 IEEE International Solid-State Circuits Conference.
Capella Microsystems, Inc. "Proximity Sensor", http://www.capellamicro.com.tw/EN/products_list.php?mode=16 copyright 2009 [retrieved Mar. 14, 2011].
Capella Microsystems, Inc. "Ambient Light Sensor (ALS)", http://www.capellamicro.com.tw/EN/products_list.php?mode=14 copyright 2009 [retrieved Mar. 14, 2011].
Optek Technology Inc. "Long Distance Reflective Switch OPB720A and OPB720B Series", http://www.optekinc.com/datasheets/opb720a-06z.pdf, Issue F.1, Jan. 2008.
Intersil, "Low Power Ambient Light and Proximity Sensor with Intelligent Interrupt and Sleep Modes", ISL29028, FN6780.1, Mar. 2, 2010.

(56) References Cited

OTHER PUBLICATIONS

Silicon Labs Si1120, "Proximity/Ambient Light Sensor With PWM Output", Rev. 1.0 Aug. 2010 Copyright 2010 by Silicon Laboratories.
Davidovic et al. "Range Finding Sensor in 90nm CMOS with Bridge Correlator Based Background Light Suppression", pp. 298-301, 978-1-4244-6664-1/10/© 2010 IEEE.
Nemecek et al., "Distance Measurement Sensor With PIN-Photodiode and Bridge Circuit", IEEE Sensors Journal, vol. 6, No. 2, pp. 391-397, Apr. 2006.
Gokturk et al, "A Time of Flight Depth Sensor—System Description, Issues and Solutions", 2004 Conference on Computer Vision and Pattern Recognition Workshop (CVPRW'04) vol. 3, Washington, D.C., USA, Jun. 27-Jul. 2, 2004.
Dongmyung Lee et al., "An 8.5Gb/s CMOSOEIC with On-chip Photodiode for Short Distance Optical Communications", 2010 IEEE International Solid-State Circuits Conference, Solid-State Circuits Conference Digest of Technical Papers (ISSCC), 2010 IEEE International, pp. 362-363, Feb. 7-11, 2010.
Office Action dated Aug. 2, 2013, in U.S. Appl. No. 12/979,276, filed Dec. 28, 2010.
Amendment dated Sep. 24, 2013, in U.S. Appl. No. 12/979,276, filed Dec. 28, 2010.
Notice of Allowance dated Feb. 14, 2014, in U.S. Appl. No. 12/979,276, filed Dec. 28, 2010.
Office Action dated Sep. 17, 2014, in Chinese Patent Appl. No. 201180015951.0 filed Jan. 25, 2011.
Amendment dated Nov. 20, 2014, in Chinese Patent Appl. No. 201180015951.0 filed Jan. 25, 2011.
Office Action dated Jun. 18, 2015 in Chinese Patent Application No. 103115498 filed Jan. 27, 2011, with English translation.
Response to Office Action filed Jul. 16, 2015 in Chinese Patent Application No. 103115498 filed Jan. 27, 2011, with English translation.
Office Action dated Nov. 4, 2015 in Chinese Patent Application No. 103115498 filed Jan. 27, 2011, with English translation.
English Abstract of Taiwanese Publication No. TW494616 published Jul. 11, 2002.
English Abstract of Chinese Publication No. CN1483268 published Mar. 17, 2004.
English Abstract of Taiwanese Publication No. TWI439716 published Jun. 1, 2014.
Response to Office Action filed Dec. 18, 2015 in Chinese Patent Application No. 103115498 filed Jan. 27, 2011, with English Translation.
Notice of Reexamination dated Nov. 11, 2015 in Chinese Patent Application No. 201180015951.0 filed Jan. 25, 2011, with English translation.
Response to Office Action filed Dec. 25, 2015 in Chinese Patent Application No. 201180015951.0 filed Jan. 25, 2011, with English translation translation.
English translation of Claims in Response to Office Action filed Dec. 25, 2015 in Chinese Patent Application No. 201180015951.0 filed Jan. 25, 2011, with English translation.
English Abstract of Chinese Publication No. CN1667432 published Sep. 14, 2015.
Decision on Reexamination dated Apr. 18, 2016 in Chinese Patent Application No. 201180015951.0 filed Jan. 25, 2011, with English Translation.
Search Report issued in Chinese Patent Application No. 201610559617.6 dated Jun. 14, 2017, 4 pages.

* cited by examiner

DISTANCE SENSING BY IQ DOMAIN DIFFERENTIATION OF TIME OF FLIGHT (TOF) MEASUREMENTS

PRIORITY CLAIM

This application is a continuation of U.S. patent application Ser. No. 12/979,726, filed on Dec. 28, 2010, entitled DISTANCE SENSING BY IQ DOMAIN DIFFERENTIATION OF TIME OF FLIGHT (TOF) MEASUREMENTS, which claims priority to U.S. Provisional Patent Application No. 61/298,895, filed on Jan. 27, 2010, entitled "ARCHITECTURE FOR A REFLECTION BASED LONG RANGE PROXIMITY AND MOTION DETECTOR HAVING AN INTEGRATED AMBIENT LIGHT SENSOR." Priority is claimed to each of the above applications, each of which is incorporated by reference herein.

DETAILED DESCRIPTION

Figure 1:
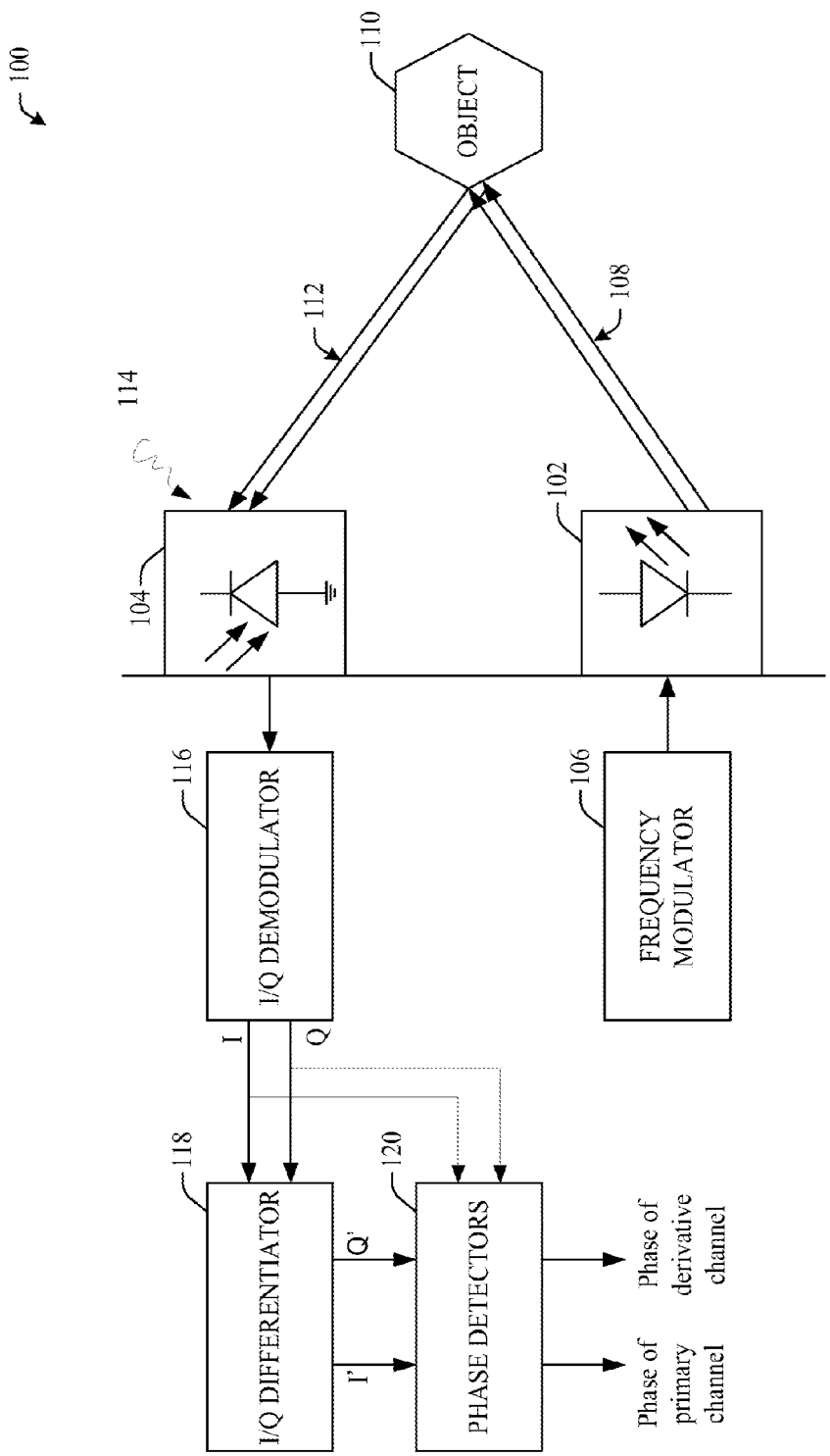
FIG. 1 illustrates an exemplary system for identifying a position of a moving object within the vision field of a long range proximity detector, independent of static interference.

A category of monolithic devices is emerging that allows electronic products to sense their environment. These include diverse devices, such as, accelerometers, monolithic gyroscopes, light sensors and imagers. In particular, light sensors are one of the simplest and cheapest, allowing their inclusion in multitudes of consumer products, for example, nightlights, cameras, cell phones, laptops etc. Typically, light sensors can be employed in a wide variety of applications related to proximity sensing, such as, but not limited to, detecting the presence and/or distance of a user to the product for the purpose of controlling power, displays, or other interface options.

Infrared (IR) proximity detectors utilize IR light to detect objects within the sense area of the IR sensor. Moreover, IR light is transmitted by an IR. Light emitting diode (LED) emitter, which reflects off of objects in the surrounding area and the reflections are sensed by a detector. Moreover, the detector can be a diode, e.g., a PIN diode, and/or any other type of apparatus that converts IR light into an electric signal. The sensed signal is analyzed to determine whether an object is present in the sense area. Some conventional systems transmit a pulse of IR light and detect whether the pulse is returned back at the pin diode. However, these conventional systems easily get confused by existing IR light in the world, e.g., ambient light, sunlight, etc. In addition, the conventional systems cannot differentiate between undesired reflections from static objects (e.g., chair, desk, soda can, etc.) and reflections from a desired object (e.g., a person, animal, etc.). Thus, to compensate for the existing IR light, the conventional systems measure the data twice; once when the IR transmitter is turned ON and an IR pulse is transmitted, and once when the IR transmitter is turned OFF. Moreover, the IR response is measured in the two cases and subtracted. Performing these calculations can be a tedious and time consuming process. Additionally, the range of such conventional detectors is only about 10-30 centimeters (cm). Further, to overcome the effects of the ambient light in a higher range, for example, range of 20-30 cm, a high amount of power needs to be transmitted by the IR LED.

The systems and methods disclosed herein provide a novel signal processing scheme for an active long-range IR distance sensor. For example, the range of the disclosed IR distance sensor can be 1-2 meters. In one aspect, the light emitted by the IR LED is modulated at a high frequency, for example 1 MHz-50 MHz. The received IR response is then demodulated by employing Quadrature amplitude demodulator (I/Q demodulation). Further, an I/Q domain differentiator or a high pass filter is utilized to actively remove the effects of all forms of static interference and the phase of the derivative of the I/Q signals is employed to calculate a position of a moving object within the vision field, independent of any static interference. It can be appreciated that although the subject specification is described with respect to IR light, the systems and methods disclosed herein can utilize most any wavelength. As an example, the subject system and/or methodology can be employed for acoustical proximity detection and/or ultrasonic range finding applications.

The subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the subject matter may be practiced without these specific details. In other instances, well-known structures and devices are shown in block diagram form in order to facilitate describing the subject innovation. Of course, those skilled in the art will recognize that many modifications may be made to this configuration without departing from the scope or spirit of the claimed subject matter.

Moreover, the word "exemplary" is used herein to mean serving as an example, instance, or illustration. Any aspect or design described herein as "exemplary" is not necessarily to be construed as preferred or advantageous over other aspects or designs. Rather, use of the word "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. In addition, the word "coupled" is used herein to mean direct or indirect electrical or mechanical coupling. Further, the terms "sense area," "vision field," "optical field," and similar terminology are utilized interchangeably in the subject application, unless context warrants particular distinction(s) among the terms.

Referring to FIG. 1, there illustrated is an example system 100 for identifying a position of a moving object within the vision field of a long range proximity detector, independent of static interference, in accordance with an aspect of the subject disclosure. In general, system 100 can be employed in most any light sensing application. For example, a laptop or personal computer can power-up (e.g., from hibernation, stand-by, etc.) on detecting that a user has entered a room. In another example, a cell phone or personal digital assistant (PDA) can switch off a display (to conserve battery life) when detected that the phone/PDA is held at the user's ear.

In one aspect, system 100 for proximity sensing based upon IR signal detection employs an IR LED 102 and an IR sensor 104. For example, the system 100 can employ a high frequency (e.g., 5 MHz) modulated LED 102 and a tuned PIN detector 104 to optimize the detection range. Moreover, most any frequency modulator 106 can be employed to modulate a signal input to the IR LED 102. As an example, the IR LED 102 has a typical peak wavelength that matches the proximity sensor spectrum, a narrow viewing angle with higher radiant intensity that can facilitate concentrating the energy that is ideal for proximity sensing. It can be appreciated that most any IR LED (or array) can be employed based on the factors, such as, but not limited to, view-angle, mechanic height, footprint, radiant intensity, current consumption, etc. Further, the IR LED 102 can emit the modulated IR signal 108 to the sensing object 110, and the IR sensor 104 can receive a portion 112 of the transmitted signal, which is reflected back from the surface of sensing object 110. The object 110 can be most any entity of interest, such as, but not limited to, a human entity, an automated component, a device, an item, an animal, etc.

Typically, the magnitude of the reflections 112 depend on the size of the object 110, the color of the object 110 and the distance of the object 110 from the IR sensor 104. As an example, a white shirt can produce higher reflections than a black shirt. In addition to the reflections 112 from the object 110, the sensor 104 can receive various other signals 114, such as, but not limited to, electrical crosstalk, optical crosstalk and/or environmental backscatter. Each of these signals represents interference to the detection of the object of interest. Of these interferences, electrical and optical crosstalk can be approximated to be relatively constant through the life time of the device, and can be calibrated at the manufacturing or development stage of the application. Environmental backscatter 114 can be received from various sources in the optical field of the sensor 104, and can include most any signal that is not of interest to the detection of the object 110. For example, objects such as a desk surface, a couch, a television display, a soda can, etc., are not useful targets, but are detected as a significant component of the signal received at the sensor 104. In one embodiment, system 100 ignores the environmental backscatter signals and isolates the signals 112 from the object 110 to identify the proximity of the object 110 from the sensor 104.

According to an aspect, system 100 utilizes Time-of-Flight (TOF) measurements, which rely on the finite speed of light. The finite speed causes a delay between the projection of an electromagnetic wave and its reflection from an object, which is proportional to the distance of the object. In system 100, the distance can be measured as a phase delay of a modulated (e.g., at 5 MHz) IR LED signal. Moreover, reflected signal is amplified and demodulated using two orthogonal carrier waves by the I/Q demodulator 116. An automatic gain control loop maintains the signal in the dynamic range of the A/D converters. The system 100 captures the real and imaginary component of the reflected signal, which can then be processed to give a phase and amplitude of the signal. Components add linearly in the I/Q domain, and therefore calibration can be performed in the linear space itself.

According to an embodiment an I/Q differentiator 118 can calculate the derivative of the I and Q signals respectively. Moreover, the I/Q differentiator 118 actively removes the effects of all forms of static interference received at the sensor 104. Further, the phase delay of the object 110 in the sensor field is preserved in the derivative of the received signal when represented in I/Q space. Static interference can include, but is not limited to, ambient light, unwanted reflections from static objects, etc. Accordingly, the phase detectors 120 can utilize the derivative of the I and Q components of a complex signal and extract the phase at which the motion occurred by utilizing the relationship between amplitude and phase. In one example the phase detector 120 can determine the phase of the primary I/Q channel and the phase of the derivate I/Q channel.

It can be appreciated that the mechanical design of system 100 can include different component selections, component placement, dimensions, glass cover characteristics, LED selections, isolation techniques between sensor 104 and LED 102, etc., to achieve an optimal proximity sensing. Further, it can be appreciated that the frequency modulator 106, I/Q demodulator 116, I/Q differentiator 118, and the phase detectors 120, can include most any electrical circuit(s) that can include components and circuitry elements of any suitable value in order to implement the embodiments of the subject innovation. Furthermore, the frequency modulator 106, I/Q demodulator 116, I/Q differentiator 118, and the phase detectors 120, can be implemented on one or more integrated circuit (IC) chips. Typically, various IR bands can be employed in imaging systems (e.g., Near IR, Mid-Wave IR and Long-Wave IR). Each band can have unique LEDs and Sensors. Oftentimes, some visible detector systems can work in the Near IR band and can include the detector integrated into the system IC. In addition, it can be appreciated that system 100 is not limited to utilizing IR light, and LEDs/sensors/detectors can utilize signals of most any wavelength.

Figure 2:
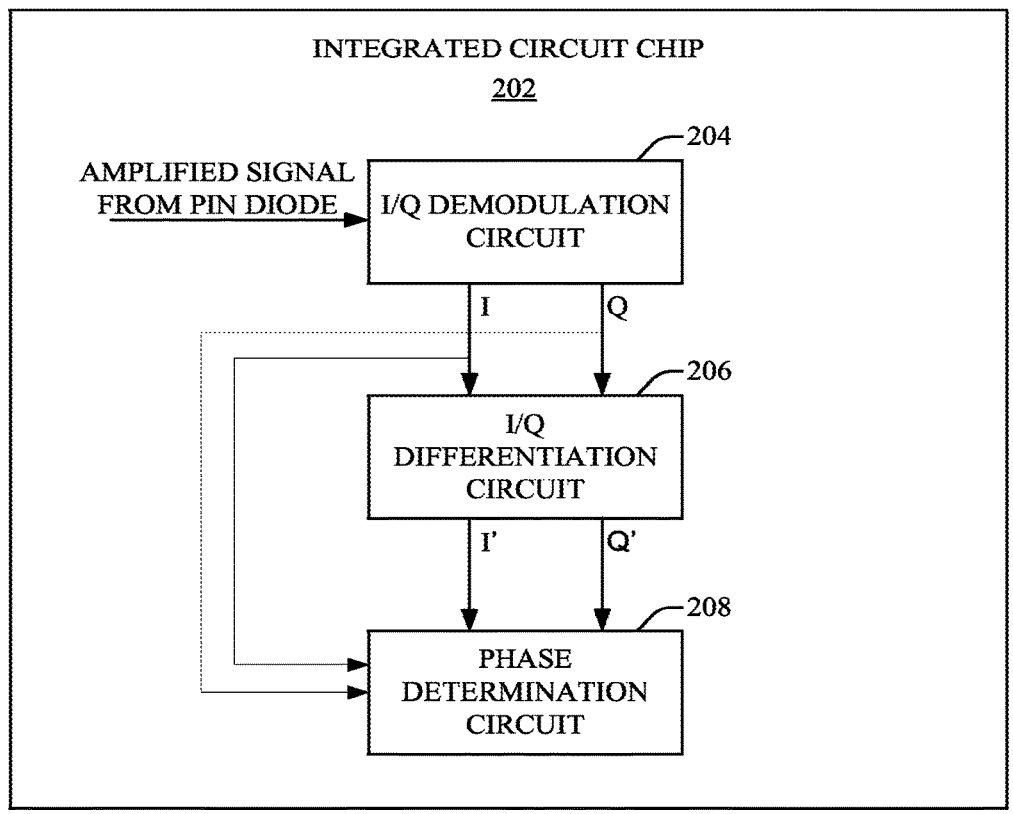
FIG. 2 illustrates an exemplary system that includes an Integrated Circuit (IC) chip, which facilitates distance sensing by employing the phase response of an active infrared (IR) proximity sensor.

Referring now to FIG. 2, there illustrated an example system 200 that includes an IC chip 202, which facilitates distance sensing, according to an aspect of the subject specification. Traditionally, distance sensing is inherently limited in its ability to capture the distance to a desired object under the presence of other objects in the optical field. However, system 200 extracts distance of moving objects, allowing accurate distance measurements in suboptimal optical environments. Moreover, IC 202 can be employed as a primary distance monitoring system and/or as a means to calibrate a traditional system. Specifically, IC 202 includes an I/Q demodulation circuit 204, I/Q differentiation circuit 206, and phase detection circuit 208, which employ the derivative of the I and Q components of a complex signal and extract the phase at which the motion occurred using the relationship between amplitude and phase. This allows background reflections from static objects to be ignored, isolating the moving target.

It can be appreciated that the I/Q demodulation circuit 204, I/Q differentiation circuit 206, and the phase detection circuit 208 can be substantially similar to demodulator 116, I/Q differentiator 118, and the phase detectors 120, and can include functionality, as more fully described herein, for example, with regard to system 100. Further, although a single IC chip (202) is illustrated in FIG. 2, it can be appreciated that multiple ICs can be employed to implement system 200.

The active IR proximity detector, disclosed herein, employs an IR LED emitter to transmit IR light, which reflects off of objects in the sense area and the reflections from the objects are sensed by a detector, e.g., a pin diode. IC 202 can analyze the sensed signal to determine motion of an object (e.g., user) in the sense area. The magnitude of the sensed signal is a function of the color, size and distance of the object. However, the phase of the returned signal depends only on the distance of the object from the sensor. As an example, the signal received by the sensor can be amplified and/or filtered, and then provided as input to the I/Q demodulation circuit 204 to facilitate identification of the phase of the sensed signal. Moreover, the IR sensor can include a filter that omits visible ambient light signals while transmitting only desired IR signals to the detector.

The I/Q demodulation circuit 204 demodulates the input signal along two different axes that are perpendicular to each other. For example, the I/Q demodulation circuit 204 can demodulate the input signal with a sine wave at zero degrees to provide the I (in-phase) channel and demodulate the input signal with another sine wave at 90 degrees to provide the Q (quadrature-phase) channel. The I and Q signals output by the I/Q demodulation circuit 204 form a vector indicating the phase of the input signal.

Further, the I/Q differentiation circuit 206 can be employed to calculate the derivative of the I and Q signals. Typically, backscatter (e.g., 114) present in the received signal can cause an error in proximity measurement. However, the reflections introduced due to backscatter are constant and thus by taking the derivative of the I and Q signals, the constant reflections caused by the backscatter can be eliminated by the I/Q differentiation circuit 206. In addition, the phase determination circuit 208 can calculate the phase of the objects moving in the field of the sensor, by employing a vector formed by the derivative of the I and Q channels. The phase can be employed to detect the position at which a motion occurred, regardless of other objects in the optical field. In an aspect, the resultant phase information can be utilized as a direct output of the system as a measure of distance, and/or can be utilized to reconstruct a static component of the signal and allow the calibration of a non-derivative TOF measurement.

The following equations and analysis explain the working of system 200 and result of the analysis below demonstrates that the position at which a motion occurred can be identified by observing the phase of the derivative of an incoming reflected signal: Consider a general complex signal x. This signal can be seen as a vector in the complex plane, with some DC (direct current) value $x_0$, and some time varying signal $x_s$ of interest imposed on it.

$$x_s = x - x_0 \quad (1)$$

$x_s$ can be expressed in terms of its magnitude ($A_s$) and phase components ($\varphi$) as follows:

$$A_s = |x_s| = |x - x_0| \quad (2)$$

$$\varphi = \text{angle}(x_s) = \text{angle}(x - x_0) \quad (3)$$

Or equivalently, $$x_s = x - x_0 = A_s e^{j\varphi} \quad (4)$$

Wherein $j = \sqrt{-1}$,
The derivative of the above expression with respect to time (t) is as follows:

$$\frac{\delta x}{\delta t} \left( \frac{\delta A_s}{\delta t} + jA_s \frac{\delta \varphi}{\delta t} \right) e^{j\varphi} \quad (5)$$

Assuming $A_s$ is only a function of $\varphi$, e.g., that there is a one to one mapping of phase and magnitude that the signal of interest $x_s$ can take. This simplifies Equation (5) to the following:

$$\frac{\delta x}{\delta t} = \frac{\delta \varphi}{\delta t} \left( \frac{\delta A_s}{\delta \varphi} + jA_s \right) e^{j\varphi} \quad (6)$$

Or in phasor notation, $$\frac{\delta x}{\delta t} = \left( \frac{\delta \varphi}{\delta t} \sqrt{\left( \frac{\delta A_s}{\delta \varphi} \right)^2 + A_s^2} \right) e^{j(\varphi + \theta(\varphi))} \quad (7)$$

$$\theta(\varphi) = \tan^{-1}\left( \frac{A_s(\varphi)}{\delta A_s / \delta \varphi} \right) \quad (8)$$

Based on this expression, the phase of the derivative of the signal x can be expressed as:

$$\angle \frac{\delta x}{\delta t} = \varphi(t) + \theta(\varphi(t)) \quad (9)$$

Wherein, $\varphi(t)$ is the angle of the original signal, and $\theta(\varphi)$ is a phase distortion term.

The phase distortion term $\theta(\varphi)$ is the additional phase added onto the phase of the original signal. As an example, if this value were to always be zero, the phase of the original signal can be recovered very easily. However, in real systems the phase distortion value is a function of the phase of the signal $\varphi$, and this relationship is determined by the relationship of the signal's magnitude and phase, as shown in Equation (8). Another approach to depict this relationship is the following:

$$\theta \approx \tan^{-1}\left( \Delta \varphi \frac{A_s}{\Delta A_s} \right) \quad (10)$$

The above depicts that the phase is related to both the change in phase, and the percent change in amplitude. The following examples illustrate how this term behaves.

(i) Magnitude Change: When there is a change in magnitude with no change in phase of the signal, the phase distortion term is dominated by $\Delta A_s \gg \Delta \varphi$. Thus the phase distortion term is:

$$\theta = 1\lim_{x \to 0} \tan^{-1}(x) = 0, \text{ if } A_s \text{ increases } \pi, \text{ if } A_s \text{ decreases}$$

(ii) Phase Change: Conversely, when there is a change in phase with no change in magnitude of the signal, the phase distortion term is dominated by $\Delta\varphi \gg \Delta A_s$. Thus the phase distortion term is:

$$\theta = \lim_{x \to 0} \tan^{-1}(1/x) = \pi/2, \text{ if } \varphi \text{ increases } -\pi/2, \text{ if } \varphi \text{ decreases}$$

To determine how the phase distortion term behaves in an active IR Time-of-Flight (TOF) sensing system (e.g., system 200), the magnitude-phase relationship for an optical signal reflected by an object in the system is identified. The amplitude of the optical signal is dependent on the color, material, and size of the target (e.g., object), but has an inverse square law dependence to distance, r, (e.g., distance travelled by the light) as long as these parameters do not change.

$$A_s = f(\text{color, material, size})/r^2 \quad (11)$$

The phase ($\varphi$) of the signal is proportional to the distance and can be calculated as:

$$\varphi = \varphi_0 + kr \quad (12)$$

Wherein, $\varphi_0$ is a phase offset due to the lack of absolute phase reference and k is a constant.
From Equations (11) and (12), the following can be determined:

$$A_s(\varphi) = f(\text{color, material, size})k^2/(k^2 r^2) \quad (13)$$
$$= A_0/(\varphi - \varphi_0)^2$$

Wherein $A_0 = f(\text{color, material, size})k^2$
This relationship can be utilized to determine the phase distortion term as a function of phase:

$$\frac{\delta A_s}{\delta \varphi} = \frac{\delta}{\delta \varphi} \frac{A_0}{(\varphi - \varphi_0)^2} \quad (14)$$
$$= -2 \frac{A_0}{(\varphi - \varphi_0)^3}$$
$$= \frac{-2}{(\varphi - \varphi_0)} A_s(\varphi)$$

$$\theta(\varphi) = \tan^{-1}\left(\frac{A_s(\varphi)}{-2A_s(\varphi)/(\varphi - \varphi_0)}\right) \quad (15)$$
$$\theta(\varphi) = \tan^{-1}\left(\frac{-(\varphi - \varphi_0)}{2}\right)$$

Applying the small angle approximation, $$\theta(\varphi) \approx -(\varphi - \varphi_0)/2 \quad (16)$$

Based on the phase of the derivative as derived in Equation (9), it can be identified that:

$$\angle \frac{\delta x}{\delta t} = \varphi + \frac{-(\varphi - \varphi_0)}{2} \quad (17)$$
$$= \frac{\varphi}{2} + \frac{\varphi_0}{2}$$

The above depicts that the phase of the derivative of a complex vector under a square law dependence of magnitude versus phase can be approximated as the same phase offset as the original signal plus half of the dynamic portion of the signal. Or in terms of distance, $$\angle \frac{\delta x}{\delta t} = \varphi_0 + \frac{kr(t)}{2} \quad (18)$$

The above result illustrates that the position at which a motion occurred can be determined by observing the phase (e.g., by employing the phase determination circuit 208) of the derivative of an incoming reflected signal. Further, since the derivative is obtained (e.g., by the I/Q differentiation circuit 206), any static objects in the sensor field are ignored in the measurement.

Referring back to the amplitude of the derivative, from Equations (7) and (14), $$\left|\frac{\delta x}{\delta t}\right| = \frac{\delta \varphi}{\delta t} \sqrt{\left(\frac{\delta A_s}{\delta \varphi}\right)^2 + A_s^2}$$
$$= \frac{\delta \varphi}{\delta t} \sqrt{\left(\frac{-2}{(\varphi - \varphi_0)} A_s\right)^2 + A_s^2}$$
$$= \frac{\delta \varphi}{\delta t} A_s \sqrt{\left(\frac{-2}{(\varphi - \varphi_0)}\right)^2 + 1}$$

The expression $\varphi - \varphi_0$ is small, and therefore dominates.

$$\left|\frac{\delta x}{\delta t}\right| \approx \frac{\delta \varphi}{\delta t} A_s \frac{2}{(\varphi - \varphi_0)}$$
$$= \frac{\delta \varphi}{\delta t} \frac{A_0}{(\varphi - \varphi_0)^2} \frac{2}{(\varphi - \varphi_0)}$$
$$= \frac{\delta \varphi}{\delta t} \frac{2 A_0}{(\varphi - \varphi_0)^3}$$

Equivalently, in terms of distance r, $$\left|\frac{\delta x}{\delta t}\right| \approx \frac{\delta r}{\delta t} \frac{2 A_0}{k^2 r^3} \quad (19)$$

Thus, it can be concluded that the amplitude of the derivative is proportional to the speed and inversely proportional to the cube of the distance.

Now referring back to FIG. 2, system 200 can be utilized to calculate the amplitude and phase of the derivative of the received signal to facilitate computing the distance of the object based at least on the above equations. In one aspect, the gain and/or sampling rate of the differentiation circuit 206 is appropriately set for the speed of the motion. Moreover, the change in the signal can be within the dynamic range of the system under the environmental backscatter. The dynamic range is reduced by the static environmental backscatter, as the automatic gain control can respond to the static environmental backscatter and/or the motion.

Figure 3:
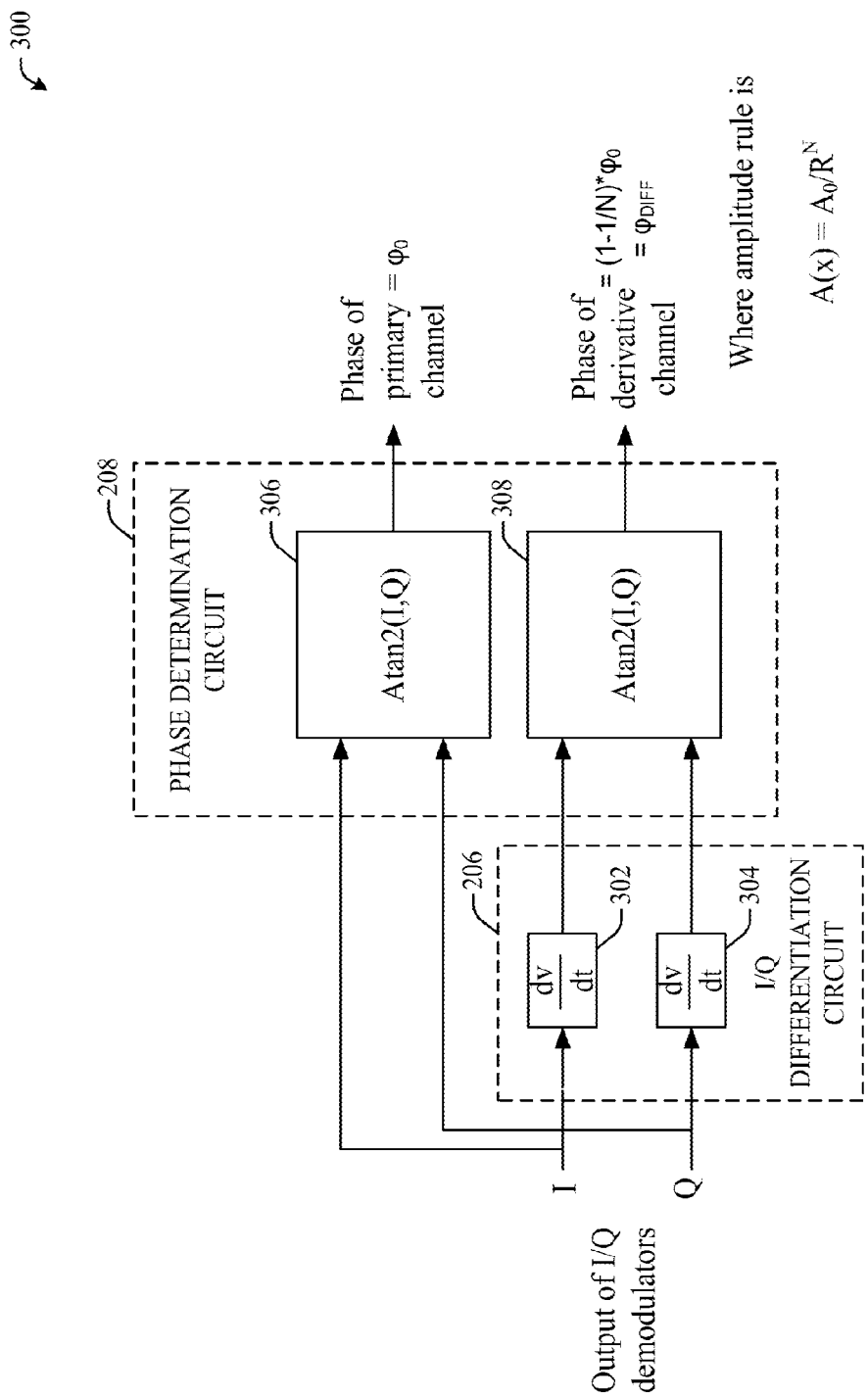
FIG. 3 illustrates an exemplary analog version system for I/Q derivative processing in accordance with an aspect of the subject innovation.

FIG. 3 illustrates an example block diagram 300 that depicts an analog version system for I/Q derivative processing in accordance with an aspect of the subject innovation. The I and Q signals obtained after demodulation (e.g., by the I/Q demodulation circuit 204) can be provided to the phase determination circuit 208. Further, the derivative of the I and Q signals obtained by the I/Q differentiation circuit 206, can also be provided to the phase determination circuit 208.

In one aspect, the dv/dt blocks (302, 304) include most any electronic circuit that can calculate the derivative of the I and Q signals with respect to time. In addition, the A tan2(I, Q) blocks (306, 308) include most any electronic circuit that can calculate the phase of the primary channel ($\varphi_0$) and the phase of the derivative channel ($\varphi_{diff}$) based on the input received from the I/Q demodulation circuit 204 and the I/Q differentiation circuit 206. The phase of the derivative channel, $\varphi_{diff}$, is equivalent to $(1-1/N)\,\varphi_0$, wherein amplitude $A(x)=A_0/R^N$. Typically, N=2 (square law attenuation with distance), so angle $\varphi_{diff}$ is half of the primary (normally measured delay phase) channel. Moreover, the phase information output by the phase determination circuit 208 can facilitate determining information related to the position of the most recent motion. This new information can be used both as a stand alone measurement, and/or as an additional calibration scheme.

Figure 4:
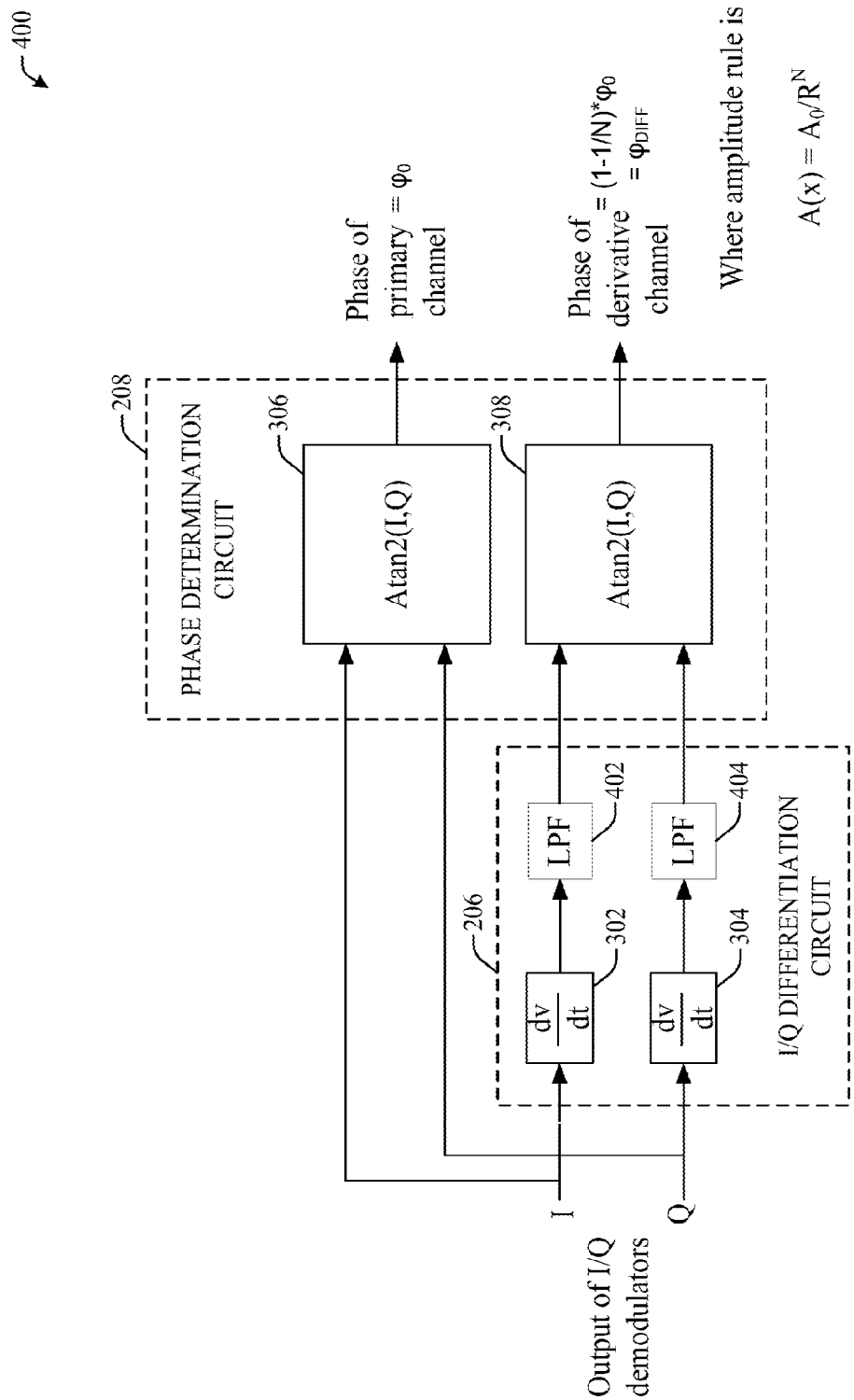
FIG. 4 illustrates an exemplary analog version system for basic I/Q derivative processing with noise control in accordance with an aspect of the disclosed specification.

Referring to FIG. 4, there illustrated is an example analog version system 400 for basic I/Q derivative processing with noise control in accordance with an aspect of the disclosed specification. It can be appreciated that the I/Q differentiation circuit 206, and the phase detection circuit 208 can include functionality, as more fully described herein, for example, with regard to system 200 and 300. Typically, in continuous time, derivatives can be very noisy. To overcome this problem, the I/Q differentiation circuit 206 can include a 'bandlimited' derivative, wherein the derivative dv/dt (302, 304) is followed by a low pass filter (LPF) (402, 404) to control noise in the system.

Figure 5:
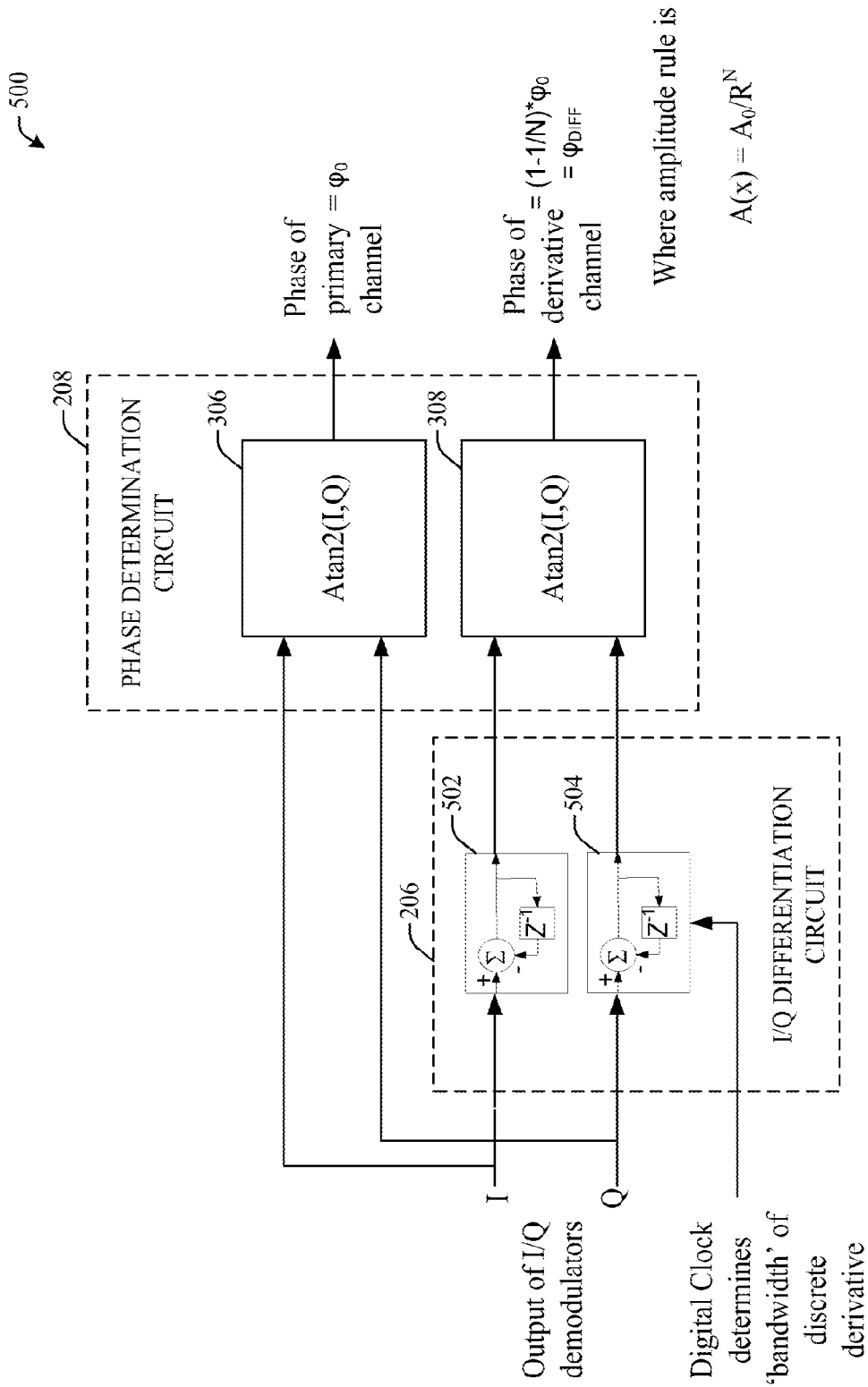
FIG. 5 illustrates an exemplary digital version system for I/Q derivative processing, according to an aspect of the subject disclosure.

FIG. 5 illustrates an example digital version system 500 for I/Q derivative processing, according to an aspect of the subject disclosure. Typically, most any analog-to-digital converters (ADCs) (not shown) can be employed to obtain the digital signals for I and Q respectively. According to an embodiment, I/Q differentiation circuit 206 can include modules 502, 504, which subtract from a current value of a signal, a delayed value of the signal. Although a unit delay ($Z^{-1}$) is illustrated in modules 502, 504, it can be appreciated that most any value delay can be utilized. The digital implementation of system 500 provides the same result for phase as the analog systems 300 and/or 400, but updates are at the digital clock times. Moreover, the Digital Clock determines 'bandwidth' of the discrete derivative.

Figure 6:
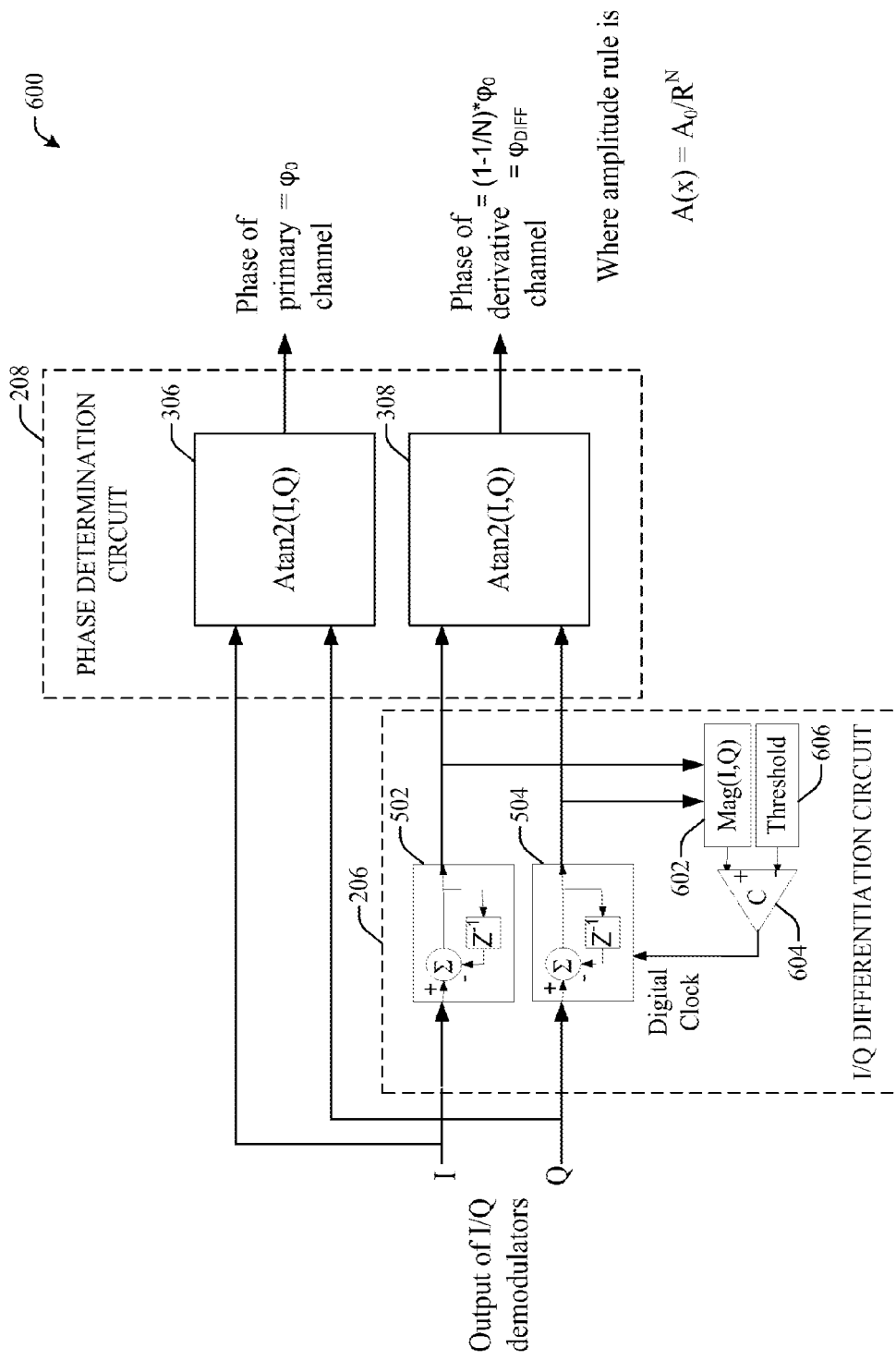
FIG. 6 illustrates an exemplary enhanced digital version system for I/Q derivative processing that employs a variable sampling rate, according to an aspect of the subject innovation.

Referring now to FIG. 6, there illustrated is example enhanced digital version system 600 for I/Q derivative processing that employs a variable sampling rate, according to an aspect of the subject innovation. The variable sampling time differentiator consists of a simple first difference that is asynchronously clocked by a trigger signal. This trigger signal is generated when the output of the first difference reaches a certain condition that assures a valid signal to noise ratio. Additional signal processing can be triggered off of this trigger signal to allow back end processing. This scheme allows the system 600 to be sensitive to all ranges of speeds.

In discrete time, significant noise can be observed during subtraction of the delayed value from the current value (of I and Q signals). Moreover, the differences are very small for normal clock frequencies and analog (sampling) noise still exists within the signal. In this case, the clock rate can be modified to allow for larger differences to accumulate before the phase calculation is made.

The I/Q differentiation circuit 206 in system 600 updates the difference equation only if the difference is large enough. This limits the 'small difference' problem and results in a variable clock rate relative to standard digital implementation. In particular, a magnitude component 602 calculates the difference between the magnitude of a current and delayed value of the I and Q signals respectively. Further, comparator 604 compares the magnitudes with a threshold value 606. As an example, the threshold value 606 can be most any value set by a user to tradeoff between noise and update rate, and/or can be dynamically adjusted. In another example, the threshold is set only slightly above the noise floor of the I/Q channels so that a full benefit of the signal-to-noise ratio (SNR) of the system can be obtained. Moreover, the digital clock takes a new sample only if the change (e.g., difference between a current and delayed value) exceeds the threshold 606. Thus, system 600 guarantees the differences to be at least as large as the threshold 606.

The difference modules 502, 504 can include a basic finite difference differentiator of the following form:

$$H(z^{-1})=1-z^{-k}$$

$$h[n]=x[n]-x[n-k]$$

If the parameter k is changed, the effective gain and/or sampling time of the differentiator can be changed. Since the magnitude of the derivative signals are not require for proximity determination, this gain can be modified without impacting downstream signal processing. Thus, k can be varied to dynamically change the gain of the differentiator (e.g., module 502, 504). As discussed supra, the differentiator (module 502, 504) takes a single sample, and waits until a signal that is significantly different from the sample, is received. Once the differentiator (module 502, 504) receives a signal that is of large enough difference to the original, the next sample is taken, for example, based on clock input from the comparator 604. System 600 can be modeled either as a variable length difference differentiator, or a variable sampling time first difference differentiator.

In one aspect, the triggering condition can be computed and tuned to optimize speed, accuracy, and SNR. The trigger signal that comes out of the comparator 604 controls the sampling of the differentiator and can also be used to clock any subsequent filtering and/or any other signal processing. This provides an asynchronous system capable of optimally shifting its gain and sampling rate that benefits from the simplicity of a synchronous signal processing system.

Figure 7:
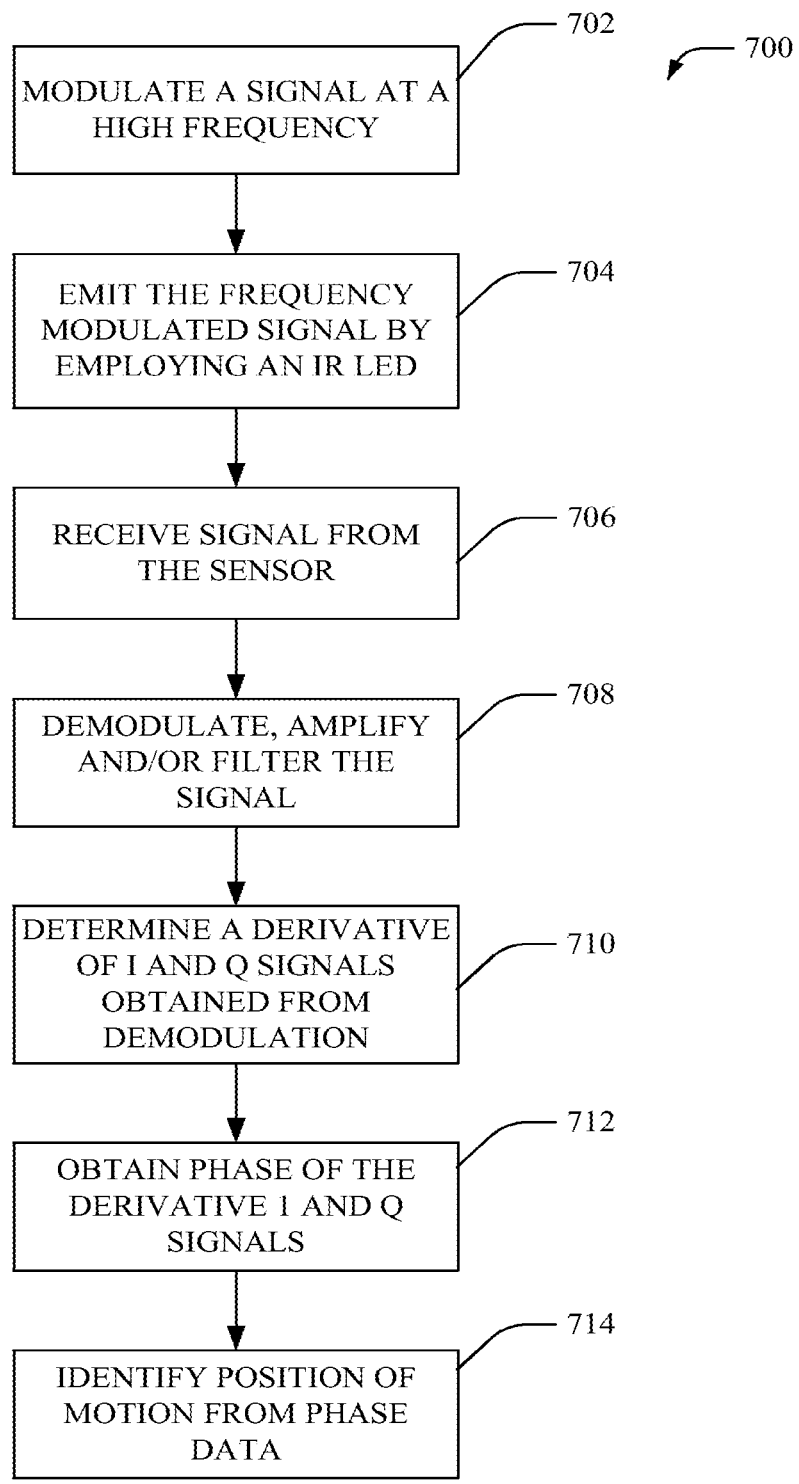
FIG. 7 illustrates an exemplary methodology that can discern distance at which motion occurred, by employing the phase response of an active IR proximity sensor.

FIG. 7 illustrates a methodology and/or flow diagram in accordance with the disclosed subject matter. For simplicity of explanation, the methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device or computer-readable storage/communications media.

FIG. 7 illustrates an example methodology 700 that can discern distance at which motion occurred, by employing the phase response of an active IR proximity sensor, while ignoring the backscatter effects of still objects in the field of view of the sensor. Typically, methodology 700 can be utilized in various applications, such as, but not limited to consumer electronic devices (e.g., cell phones, laptops, media players, gaming systems, night-vision systems, etc.), mechanical systems (e.g., door/window mechanism), industrial automation systems, robotics, etc.

At 702, a signal, for example, input to an IR LED, can be modulated at a high frequency (e.g., 1 MHz-50 MHz). As an example, most any frequency modulation technique can be employed for modulation. At 704, the modulated signal can be emitted by the IR LED. Typically, the range of the IR LED can be selected based on the application (e.g., 1-2 meters). The emitted IR signal is reflected back from objects (moving and/or stationary) within the optical field and the reflected signals can be received at an IR sensor, along with ambient light (e.g., sunlight, florescent lights, lamps, bulbs, etc.). At 706, the signal is received from the sensor and at 708 the signal can be demodulated, amplified and/or filtered. Typically, I/Q demodulation can be performed on the received signal. Moreover, the received signal is demodulated along two perpendicular axes to generate I and Q signals.

Further, at 710 a derivative of the I and Q signals can be determined, for example, by utilizing an I/Q domain differentiation or a high pass filter. Moreover, the differentiation removes the effects of all forms of static interference (e.g., ambient light and/or reflections from stationary objects). Furthermore, at 712, the phase of the derivative of the I and Q signals can be obtained. At 714, the phase data can be employed to identify position of motion within the vision field, independent of any static interference.

Figure 8:
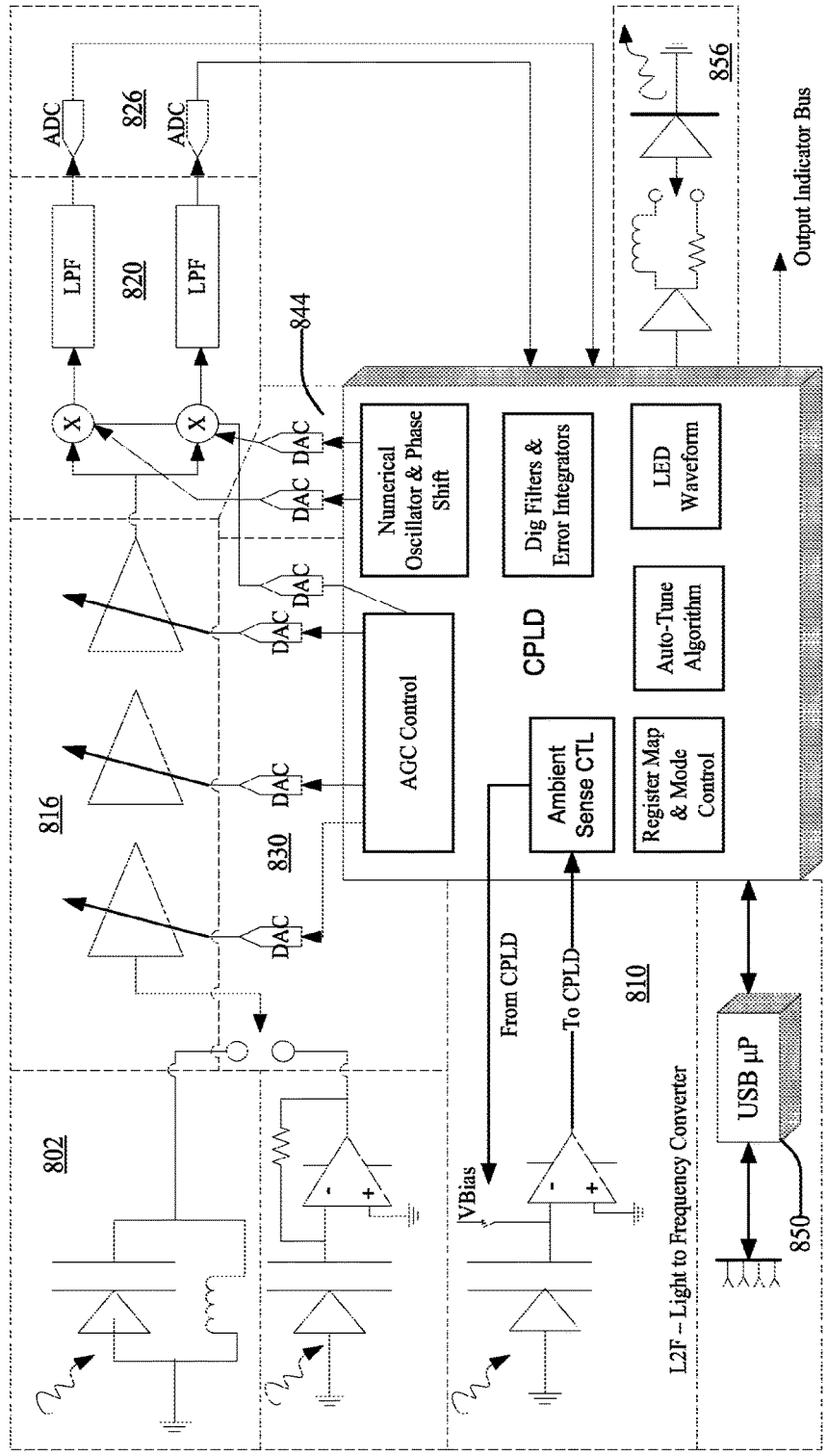
FIG. 8 illustrates an exemplary functional block diagram for the architecture of the subject innovation.

In order to provide additional context for various aspects of the subject specification, FIG. 8 illustrates an exemplary functional block diagram for the architecture 800 of the subject innovation. In one aspect, the systems (e.g., 300-600) disclosed herein can be employed in a reflection based proximity and motion detector with an integrated ambient light sensor (ALS) depicted in FIG. 8. The architecture 800 includes a LED and associated driver circuitry, a photodiode sensor, an analog front end and signal processing, data conversion circuitry, digital control and signal processing, interface circuitry and results display. The architecture 800 adaptively optimizes sensitivity and power for a given environment. Moreover, the architecture 800 derives significant performance improvements from its novel ALS structure, and its light emitting diode (LED) driver circuitry is much more efficient than the conventional resistive drive.

According to an aspect of the subject innovation, the architecture 800 includes a Resonant Front End 802, which includes a Trans-Impedance Resonator (TIR). In the architecture 800, the TIR 802 is used in place of the Trans-Inductance Amplifier (TIA), which is conventionally used. Although the TIR 802 plays the same role as a conventional TIA, the TIR 802 gives an order of magnitude improvement in achievable Signal-to-Noise-Ratio (SNR) due to its band-pass nature (e.g., TIR 802 includes an inductor and a capacitor), which allows for an increased range of sensing. One of ordinary skill in the art will appreciate that the capacitor of the TIR can include the capacitance of the photodiode that is being resonated. The band-pass nature of the TIR 802 causes the architecture 800 to operate over a narrow band of frequencies, which allows for little noise compared to the wide band TIA.

According to another aspect of the subject innovation, the novel Ambient Light Sensor (ALS) 810 uses a light to frequency converter based on a relaxation oscillator instead of the conventional TIA. A relaxation oscillator is an oscillator based upon the relaxation behavior of a physical system. An exemplary implementation for the relaxation oscillator of the subject innovation can be done by connecting the inverting input of an Operational Amplifier (Op Amp) to a fixed bias voltage via a switch and also the photodiode, with the non-inverting input connected to ground. When the switch to the fixed bias voltage is opened, the photodiode will discharge towards ground. The rate of discharge will depend on the photodiode current, which is a measure of the incident ambient light. When the photodiode is discharged to ground, the Computer Programmable Logic Device (CPLD) resets the oscillator by switching back in the bias voltage. The CPLD counts the number of cycles that the photodiode takes to discharge, and thus can estimate the ambient light intensity incident on the photodiode. The ALS 810 can be used for ambient light sensing applications and the TIR 802 can be used for proximity and motion sensing applications.

The output of the Front End 802 is subjected to multiple stages of voltage gain 816 to maximize the SNR of the output signal. The voltage gain is adaptively set based on the magnitude of the signal received from the Front End 802, which is potentially made up of both measureable interferers such as a backscatter and a crosstalk from the LED, and also the desired signal to be measured. The interferers are dynamically calibrated out of the measurement to improve the sensitivity. According to another aspect of the subject innovation, the LED drive circuitry 856 uses an inductive drive, which results in a significant efficiency improvement over the conventional resistive drive.

The architecture 800 also includes a Quad Demodulator (e.g., I/Q demodulator 116, I/Q demodulation circuit 204) with low pass filters (LPFs) 820, dual [I & Q] Analog to Digital Converters (ADCs) 826, Digital to Analog Converters (DACs) 830 driven by the bias voltage provided by the Automatic Gain Control module, Oscillator DACs 844 for I and Q carriers, the Universal Serial Bus (USB) processor for Control Interface, and the Computer Programmable Logic Device (CPLD) that include several modules. One of ordinary skill in the art will appreciate that I and Q relate to In-Phase and Quadrature demodulation components.

QAM is both an analog and a digital modulation scheme. Moreover, QAM is a modulation scheme in which two sinusoidal carriers, one exactly 90 degrees out of phase with respect to the other, are used to transmit data over a given physical channel. Since the orthogonal carriers occupy the same frequency band and differ by a 90 degree phase shift, each can be modulated independently, transmitted over the same frequency band, and separated by demodulation at the receiver. Thus, QAM enables data transmission at twice the rate of standard pulse amplitude modulation (PAM) without any degradation in the bit error rate (BER). In one example a numerically controlled oscillator (NCO) can be employed to design a dual-output oscillator that accurately generates the in-phase and quadrature carriers used by a QAM modulator and/or demodulator. A filter, for example, a raised cosine finite impulse response (FIR) filter can be utilized to filter the data streams before modulation onto the quadrature carriers.

The in-phase and quadrature demodulated components are created by multiplying the signal by both a carrier signal, and also a signal 90 degrees out of phase of that carrier, and low pass filtering the result (820 in FIG. 8). The resultant I and Q are a baseband representation of the received signal. Moreover, as described more fully herein with respect to systems 100-600, the phase of the derivative of the I and Q channels can be obtained, which is indicative of the distance of the target to be calculated. In one example, the I/Q differentiation circuit 206 can generate the derivative of the I and Q components and the phase determination circuit 208 can determine phase of the derivate I and Q components. Further, the position of a moving object can be accurately identified based on the phase data. Typically, the resultant phase information can be used as a direct output of the system as a measure of distance/position, and/or can be used to reconstruct the static component of the signal and allow the calibration of a non-derivative TOP measurement.

The architecture 800 of the subject innovation can be used in many applications including computers, automotive, industrial, television displays and others. For example, the architecture 800 can be used to detect that a user has entered the room and automatically cause a laptop computer in hibernation mode to wake up and enter into the active mode so that the user can use it. In another example, the architecture 800 of the subject innovation can be used to automatically and adaptively adjust the intensity of a liquid crystal display (LCD) based on the ambient lighting conditions. According to an aspect of the subject innovation, the architecture 800 can perform motion and proximity sensing at a range of up to 1-2 meters. According to another aspect of the subject innovation, the architecture 800 of the subject innovation can perform its operations by using less than twenty milli-watts (mW) of power.

In one embodiment of the subject innovation, the entire architecture 800 can be implemented in a single integrated circuit chip (IC). In another embodiment of the subject innovation, all components of the architecture 800 can be implemented in the IC except for the two inductors for the TIR 802 and the LED driver circuitry 856 and the LED, which can be implemented outside the IC. In yet another embodiment of the subject innovation, all components of the architecture 800 can be implemented in the IC except for the TIR 802 inductor, the LED and the inductor and the resistor for the LED driver circuitry, which can be implemented outside the IC. In still another embodiment of the subject innovation, various components of the architecture 800 can be located inside or outside the IC.

What has been described above includes examples of the subject innovation. It is, of course, not possible to describe every conceivable combination of components or methodologies for purposes of describing the claimed subject matter, but one of ordinary skill in the art may recognize that many further combinations and permutations of the subject innovation are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable medium having computer-executable instructions for performing the acts and/or events of the various methods of the claimed subject matter.

The aforementioned systems/circuits/modules have been described with respect to interaction between several components. It can be appreciated that such systems/circuits/ modules and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A method for determining at least one of a distance or presence of one or more moving objects, the method comprising:

(a) receiving in-phase (I) and quadrature-phase (Q) signals that were produced by performing quadrature demodulation of a sensor signal indicative of a portion of a light signal that was reflected from one or more objects;

(b) determining derivatives of the in-phase (I) and quadrature-phase (Q) signals;

(c) determining a phase of the derivatives of the in-phase (I) and quadrature-phase (Q) signals; and (d) determining at least one of a distance or presence of one or more moving objects in dependence on the phase of the derivatives of the in-phase (I) and quadrature-phase (Q) signals.

2. The method of claim 1, wherein:

step (b) is performed using analog circuitry configured to determine derivatives of the in-phase (I) and quadrature-phase (Q) signals.

3. The method of claim 2, wherein:

step (b) includes low pass filtering outputs of the analog circuitry configured to determine derivatives of the in-phase (I) and quadrature-phase (Q) signals to thereby filter out at least some noise introduced by the analog circuitry.

4. The method of claim 1, wherein the in-phase (I) and quadrature phase (Q) signals received at step (a) are analog signals, and wherein step (b) includes:

converting the in-phase (I) and quadrature-phase (Q) signals into digital in-phase (I) and quadrature-phase (Q) signals, respectively;

determining the derivative of the digital in-phase (I) signal by subtracting a delayed value of the digital in-phase (I) signal from a current value of the digital in-phase (I) signal; and determining the derivative of the digital quadrature-phase (Q) signal by subtracting a delayed value of the digital quadrature-phase (Q) signal from a current value of the digital quadrature-phase (Q) signal.

5. The method of claim 4, wherein the subtracting are performed in accordance with a variable sampling rate that ensures that results of the subtracting are at least as large as a threshold value.

6. The method of claim 1, wherein the in-phase (I) and quadrature phase (Q) signals received at step (a) are digital signals, and wherein step (b) includes:
   determining the derivative of the in-phase (I) signal by subtracting a delayed value of the in-phase (I) signal from a current value of the in-phase (I) signal; and
   determining the derivative of the quadrature-phase (Q) signal by subtracting a delayed value of the quadrature-phase (Q) signal from a current value of the quadrature-phase (Q) signal.

7. The method of claim 6, wherein the subtracting are performed in accordance with a variable sampling rate that ensures that results of the subtracting are at least as large as a threshold value.

8. A subsystem for use with a further subsystem, the further subsystem including a driver configured to produce a drive signal that drives a light emitting element to thereby cause a light signal to be emitted, an optical sensor configured to produce a sensor signal that is indicative of a portion of the light signal that reflects from one or more objects and is incident on the optical sensor and a demodulator configured to perform quadrature demodulation of the sensor signal to produce in-phase (I) and quadrature phase (Q) signals, the subsystem comprising:
   a differentiator configured to determine derivatives of the in-phase (I) and quadrature phase (Q) signals from the demodulator;
   a phase detector configured to determine a phase of the derivatives of the in-phase (I) and quadrature phase (Q) signals; and
   circuitry configured to use the phase of the derivatives of the in-phase (I) and quadrature phase (Q) signals to determine at least one of a distance or presence of one or more moving objects within a sensor field of the optical sensor.

9. The subsystem of claim 8, wherein when there are one or more moving objects and one or more static objects within a sensor field of the optical sensor:
   the derivatives of the in-phase (I) and quadrature-phase (Q) signals determined by the differentiator are indicative of reflections from one or more moving objects and are generally not indicative of reflections from one or more static objects within the sensor field of the optical sensor.

10. The subsystem of claim 8, further comprising:
   circuitry configured to use the phase of the derivatives of the in-phase (I) and quadrature phase (Q) signals to calibrate further circuitry configured to determine at least one of a distance or presence of one or more moving objects based on non-differentiated in-phase (I) and quadrature phase (Q) signals;
   wherein the calibration compensates for one or more static objects within a sensor field of the optical sensor.

11. The subsystem of claim 8, wherein the differentiator comprises analog circuitry configured to determine derivatives of the in-phase (I) and quadrature phase (Q) signals.

12. The subsystem of claim 11, wherein the differentiator further comprises a low pass filter configured to low pass filter outputs of the analog circuitry configured to determine derivatives of the in-phase (I) and quadrature phase (Q) signals to thereby filter out at least some noise introduced by the analog circuitry.

13. The subsystem of claim 8, wherein the differentiator includes:
   an analog-to-digital converter (ADC) configured to convert the in-phase (I) signal produced by the demodulator into a digital in-phase (I) signal;
   an analog-to-digital converter (ADC) configured to convert the quadrature-phase (Q) signal produced by the demodulator into a digital quadrature-phase (Q) signal;
   circuitry configured to subtract a delayed value of the digital in-phase (I) signal from a current value of the digital in-phase (I) signal; and
   circuitry configured to subtract a delayed value of the digital quadrature-phase (Q) signal from a current value of the digital quadrature-phase (Q) signal.

14. The subsystem of claim 13, wherein the circuitry configured to subtract a delayed value of the digital in-phase (I) signal from a current value of the digital in-phase (I) signal, and the circuitry configured to subtract a delayed value of the digital quadrature-phase (Q) signal from a current value of the digital quadrature-phase (Q) signal, each perform said corresponding subtraction in accordance with a fixed sampling rate.

15. The subsystem of claim 13, wherein the circuitry configured to subtract a delayed value of the digital in-phase (I) signal from a current value of the digital in-phase (I) signal, and the circuitry configured to subtract a delayed value of the digital quadrature-phase (Q) signal from a current value of the digital quadrature-phase (Q) signal, each perform said corresponding subtraction in accordance with a variable sampling rate that ensures that results of the subtracting are at least as large as a threshold value.

16. The method of claim 1, further comprising:
   (e) using the phase of the derivatives of the in-phase (I) and quadrature-phase (Q) signals to calibrate circuitry that determines at least one of a distance or presence of one or more moving objects based on non-differentiated in-phase (I) and quadrature-phase (Q) signals in a manner that compensates for one or more static objects.

* * * * *